United States Patent
Jung et al.

(10) Patent No.: US 9,974,936 B2
(45) Date of Patent: May 22, 2018

(54) METHOD FOR MANUFACTURING MICROSTRUCTURE USING NEGATIVE PRESSURE AND MICROSTRUCTURE MANUFACTURED THEREFOR

(71) Applicant: JUVIC INC., Seoul (KR)

(72) Inventors: Hyung Il Jung, Seoul (KR); Hui Suk Yang, Seoul (KR)

(73) Assignee: JUVIC INC., Seoul (KR)

( * ) Notice: Subject to any disclaimer, the term of this patent is extended or adjusted under 35 U.S.C. 154(b) by 322 days.

(21) Appl. No.: 14/426,598

(22) PCT Filed: Feb. 20, 2014

(86) PCT No.: PCT/KR2014/001373
§ 371 (c)(1),
(2) Date: Mar. 6, 2015

(87) PCT Pub. No.: WO2014/129816
PCT Pub. Date: Aug. 28, 2014

(65) Prior Publication Data
US 2015/0224293 A1    Aug. 13, 2015

(30) Foreign Application Priority Data
Feb. 22, 2013 (KR) ........................ 10-2013-0019247

(51) Int. Cl.
*A61M 37/00* (2006.01)
*A61K 9/00* (2006.01)
(Continued)

(52) U.S. Cl.
CPC ....... *A61M 37/0015* (2013.01); *A61K 9/0021* (2013.01); *B81C 1/00111* (2013.01);
(Continued)

(58) Field of Classification Search
CPC ........... A61M 25/06; B05D 5/00; A61C 11/00
(Continued)

(56) References Cited

U.S. PATENT DOCUMENTS 6,325,628 B1 * 12/2001 Morgan ............... A61C 8/0048
433/173
2008/0157421 A1    7/2008 Mukai et al.
(Continued)

FOREIGN PATENT DOCUMENTS

| KR | 1020100038071 | | 4/2010 |
| KR | 1020110012986 | A1 | 2/2011 |
| KR | 1020110110665 | | 10/2011 |

OTHER PUBLICATIONS

Nissen et al., Forming and Shaping Processes Vacuum Forming (Vacuum Formning), 1996, Institut for Procestekknik Danmarks Tekniske Universitet, http://polynet.dk/ingpro/forming/vacuum.htm.*

*Primary Examiner* — Dah-Wei D Yuan
*Assistant Examiner* — Andrew Bowman
(74) *Attorney, Agent, or Firm* — Clark & Elbing LLP; Susan M. Michaud

(57) ABSTRACT

The present invention is directed to a method for manufacturing a microstructure, the method comprising: (a) placing a viscous composition on a substrate; and (b) applying negative pressure to the viscous composition to induce an extension of the viscous composition, thereby forming a microstructure, and a microstructure manufactured therefor. According to the present invention, a microstructure can be formed without performing a heat treatment by applying a negative pressure. Consequently, it is possible to mount on a microstructure various materials that are sensitive to heat and easily damaged or degenerated. According to the present invention, a microstructure can be manufactured in a non-contacting manner, that is, without being contacted with (Continued)

conventionally used another structure such as a mold or filler. This leads to overcome a loss caused during a process of separating a microstructure in contact or a cutting process involving a physical destruction after the completion of molding a microstructure and limit on the production yield.

22 Claims, 16 Drawing Sheets

(51) Int. Cl.
  *B81C 1/00* (2006.01)
  *A61B 5/00* (2006.01)
  *A61B 17/20* (2006.01)
(52) U.S. Cl.
  CPC ............. *A61B 5/685* (2013.01); *A61B 17/205* (2013.01); *A61M 2037/0053* (2013.01); *A61M 2207/00* (2013.01)
(58) Field of Classification Search
  USPC ................. 427/2.28, 2.3; 604/21; 433/173
  See application file for complete search history.

(56) References Cited

U.S. PATENT DOCUMENTS

| | | | |
|---|---|---|---|
| 2008/0213461 A1* | 9/2008 | Gill | A61K 9/0021 427/2.3 |
| 2008/0299290 A1* | 12/2008 | Kirby | A61M 37/0015 427/2.28 |

* cited by examiner

METHOD FOR MANUFACTURING MICROSTRUCTURE USING NEGATIVE PRESSURE AND MICROSTRUCTURE MANUFACTURED THEREFOR

TECHNICAL FIELD

This application claims priority to and the benefit of Korean Patent Application No. 10-2013-0019247 filed in the Korean Intellectual Property Office on Feb. 22, 2013, the entire contents of which are incorporated herein by reference.

The present invention relates to a method for manufacturing microstructure using negative pressure and microstructure manufactured therefor.

BACKGROUND ART

Despite the development of numerous drugs and therapeutic agents for treating diseases, problems involving the passage of biological barriers (e.g., skin, oral mucosa, and brain-blood barrier) and the efficiency of drug delivery still remain to be improved in view of delivering the drugs into the body.

Generally, drugs are orally administered in a dosage form of a tablet or capsule, but numerous drugs can be effectively delivered through only the above administration manner since they are digested or absorbed in the gastrointestinal tract or lost due to hepatic mechanisms. Moreover, some drugs cannot be efficiently diffused when passed through the intestinal mucosa. Also, patient compliance is problematic (e.g., patients who need take drugs at predetermined intervals or cannot take drugs).

Another general technique for drug delivery is to use conventional needles. While this technique is more effective than oral administration, it causes pain at the injection sites, local damage to the skin, bleeding, or infections at the injection sites.

In order to solve the above problems, several microstructures including microneedles have been developed. Recently developed microneedles have been used for in vivo delivery of drugs, blood collecting, detection of in vivo analytes, and the like.

The microneedles are characterized by painless skin penetration and causing no wounds unlike existing needles, and the diameter at the top for the minimum sharpness is important in the painless skin penetration. In addition, the microneedle is required to have a sufficient physical hardness since it needs to pass through the stratum corneum of 10-20 µm, which is the thickest barrier in the skin. The microneedle needs to also have an appropriate length in order to improve the efficiency of drug delivery by arriving in capillary vessels.

As for the method using a mold (1) among existing microneedle manufacturing methods, a microneedle was manufactured by filling a biodegradable solution in a microneedle-shaped mold and then hardening and separating the mold (Jung-Hwan Park et al., Biodegradable polymer microneedles: Fabrication, mechanics and transdermal drug delivery, *Journal of Controlled Release* 104:51-66 (2005)).

In addition, as for the microneedle manufacturing method through contact and stretching of an existing viscous solution, a microneedle was molded by contacting the viscous solution with a pillar structure or a substrate, followed by stretching (Kwang Lee and Hyungil Jung, Drawing lithography for microneedles: A review of fundamentals and biomedical applications, *Biomaterials* 33:7309-7326 (2012)). This manufacturing method includes a procedure of binding the viscous solution to a supporter through the contact and then performing stretching, and a procedure of performing solidification in a microneedle shape and then cutting the weakest portion between the microneedle and the pillar structure or substrate through physical destruction.

The existing microneedle manufacturing methods as described above are characterized in that the microneedle is molded through contact with a solution. The existing microneedle manufacturing methods have limitations, such as the loss during the separation procedure after the contact or the restriction of surface characteristics that can be manufactured, due to making the contact.

Besides, the existing methods for manufacturing a microstructure such as a microneedle include a method using air blowing, which is disclosed in WO 2010-039006, and a method using three-dimensional downward flow, which is disclosed in WO 2009-154411.

Skin is composed of stratum corneum (<20 µm), epidermis (<100 µm), and dermis (300 to 2,500 µm), on the outer layer thereof. Therefore, in order to deliver drugs and skin care ingredients to a specific layer of the skin without pain, the microneedle needs to be manufactured to have a top diameter of within 30 µm, an effective length of 200 to 2,000 µm, and a sufficient hardness to penetrate the skin, which is also effective in delivering the drugs and skin care ingredients. In addition, in order to deliver drugs or skin care ingredients through a biodegradable solid microneedle, process steps that may destroy activities of the drugs and skin care ingredients, such as high-heat treatment, treatment with an organic solvent, and the like, need to be excluded from the microneedle manufacturing process. However, there are no conventional techniques sufficiently satisfying these requirements.

Therefore, novel methods for manufacturing microstructures capable of solving the above-mentioned problems have been continuously required.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

DETAILED DESCRIPTION OF THE INVENTION

Technical Problem

The present inventors have endeavored to develop a novel method for manufacturing a microstructure, the method solving the above-mentioned problems in the conventional art and having the following advantages: (i) providing a microstructure having a micro-unit diameter, a sufficient extent of effective length, and a sufficient hardness; (ii) excluding processes that may destroy activities of drugs or skin care ingredients, such as high-heat treatment, treatment with an organic solvent, and the like; (iii) a quick manufacturing process; (iv) suitable for mass production; and (v) providing microstructures with a predetermined quality. As a result of research, it was confirmed that a microstructure having the above-mentioned advantages can be provided through a process in which a negative pressure is applied to a viscous composition.

Accordingly, an aspect of the present invention is to provide a method for manufacturing a microstructure.

Another aspect of the present invention is to provide a microstructure.

Other purposes and advantages of the present disclosure will become clarified by the following detailed description of the invention, claims, and drawings.

Technical Solution

In accordance with an aspect of the present invention, there is provided a method for manufacturing a microstructure, the method comprising:

(a) placing a viscous composition on a substrate; and (b) applying negative pressure to the viscous composition to induce an extension of the viscous composition, thereby forming a microstructure.

The present inventors have endeavored to develop a novel method for manufacturing a microstructure, the method solving the above-mentioned problems in the conventional art and having the following advantages: (i) providing a microstructure having a micro-unit diameter, a sufficient extent of effective length, and a sufficient hardness; (ii) excluding processes that may destroy activities of drugs or skin care ingredients, such as high-heat treatment, treatment with an organic solvent, and the like; (iii) a quick manufacturing process; (iv) suitable for mass production; and (v) providing microstructures with a predetermined quality. As a result of research, it was confirmed that a microstructure having the above-mentioned advantages can be provided through a process in which a negative pressure is applied to a viscous composition.

The method of the present invention will be described step by step in detail in the following.

Step (a): Preparation of Viscous Composition on Substrate

Herein, a viscous material is used to manufacture a microstructure. As used herein, the term "viscous composition" refers to any composition that can be shape-transformed by a negative pressure used herein to form a microstructure.

The viscosity of the viscous material may be variously changed depending on kinds, concentrations, or temperatures of materials contained in the composition or by adding a viscosity modifying agent or the like, and may be appropriately adjusted to suit the purpose of the present invention. The viscosity of the viscous composition may be adjusted by the inherent viscosity of a viscous material, and may be adjusted by further adding a viscosity modifying agent to the viscous composition.

For example, a viscosity modifying agent that is conventionally used in the art, such as hyaluronic acid or a salt thereof, polyvinyl pyrrolidone, a cellulosic polymer, dextran, gelatin, glycerin, polyethylene glycol, polysorbate, propylene glycol, povidone, carbomer, ghatti gum, guar gum, glucomannan, glucosamine, dammer resin, rennet casein, locust bean gum, microfibrillated cellulose, psyllium seed gum, xanthan gum, arabino galactan, Arabic gum, alginates, gelatin, gellan gum, carrageenan, karaya gum, curdlan, chitosan, chitin, tara gum, tamarind gum, tragacanth gum, furcelleran, pectin, or pullulan, may be added to a main ingredient of the microstructure, e.g., a composition containing a biocompatible composition, may be added to the viscous composition, thereby adjusting the viscosity of the composition to suit the purpose of the present invention. Preferably, the viscous composition used herein exhibits viscosity of 200,000 cSt or lower.

According to an embodiment of the present invention, the viscous composition used herein contains a biocompatible or biodegradable composition. As used herein, the term "biocompatible material" refers to any material that is substantially non-toxic to the human body, chemically inactive, and has no immunogenicity. As used herein, the term "biodegradable material" refers to a material that is in vivo biodegradable by body fluids or microorganisms.

According to an embodiment of the present invention, a viscous composition includes hyaluronic acid and its salts, polyvinylpyrrolidone, cellulose polymer (for example, hydroxypropyl methylcellulose, hydroxyalkyl cellulose, hydroxyethyl cellulose, hydroxypropyl cellulose, ethyl hydroxyethyl cellulose, alkyl cellulose and carboxymethyl cellulose), dextran, gelatin, glycerin, polyethyleneglycol, polysorbate, propyleneglycol, povidone, carbomer, gum ghatti, guar gum, glucomanan, glucosamine, dammer resin, rennet casein, locust bean gum, microfibrillated cellulose, psyllium seed gum, xanthan gum, arabino galactan, arabic gum, alginic acid, gelatin, gellan gum, carrageenan, karaya gum, curdlan, chitosan, chitin, tara gum, tamarind gum, tragacanth gum, furcelleran, pectin and pullulan.

Optionally, the viscous composition may contain a biocompatible and/or biodegradable material as a main component.

The biocompatible and/or biodegradable materials include polyester, PHAs, poly($\alpha$-hydroxy acid, poly($\beta$-hydroxy acid, poly(3-hydroxybutyrate-co-valerate; PHBV), poly(3-hydroxyproprionate; PHP), poly(3-hydroxyhexanoate; PHH), poly(4-hydroxy acid), poly(4-hydroxybutyrate), poly(4-hydroxy valerate), poly(4-hydroxyhexanoate), poly(esteramide), polycarprolactone, polylactide, polyglycoride, poly(lactide-co-glycoride; PLGA), polydioxanone, polyorthoester, polyetherester, polyanhydride, poly(glycolacid-co-trimethylene carbonate), polyphosphoester, polyphosphoester urethane, poly(amino acid), polycyanoacrylate, poly(trimethylene carbonate), poly(iminocarbonate), poly(tyrosine carbonate), polycarbonate, poly(tyrosine arylate), polyalkylene oxalate, polyphosphagens, PHA-PEG, ethylene vinyl alchol copolymer (EVOH), polyurethane, silicon, polyester, polyolefin, polyisobutylene, ethylene-alphaolefin copolymer, stylene-isobutylene-stylene triblock copolymer, acryl polymer and copolymer, vinyl halide polymer and copolymer, polyvinyl chloride, polyvinyl ether, polyvinyl methyl ether, polyvinyliden halide, polyvinyliden fluoride, polyvinyliden chloride, polyfluoroalkene, polyfluoroalkene, polyacrylonitrile, polyvinyl ketone, polyvinyl aromatics, polystylene, polyvinyl ester, polyvinyl acetate, ethylene-methyl metacrylate copolymer, acrylonitrile-stylene copolymer, ABS resin and ethylene-vinyl acetate copolymer, polyamide, alkyid resin, polyoxymethylene, polyimide, polyether, polyacrylate, polymetacrylate, polyacrylate-co-malic acid, chitosan, dextran, cellulose, heparin, hyaluronic acid, alginate, inulin, starch or glycogen, preferably polyester, polyhydroxyalkanoate (PHAs), poly($\alpha$-hydroxy acid), poly($\beta$-hydroxy acid), poly(3-hydroxybutylate-co-valerate; PHBV), poly(3-hydroxyproprionate; PHP), poly(3-hydroxyhexanoate; PHH), poly(4-hydroxy acid), poly(4-hydroxybutylate), poly(4-hydroxy valerate), poly(4-hydroxyhexanoate), poly(esteramide), polycarprolactone, polylactide, polyglycoride, poly(lactide-co-glycoride; PLGA), polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(iminocarbonate), poly(tyrosine carbonate), polycarbonate, poly(tyrosine arylate), polyalkylene oxalate, polyphosphagens, PHA-PEG, chitosan, dextran, cellulose, heparin, hyaluronic acid, alginate, inulin, starch and glycogen.

According to an embodiment of the present invention, the viscous composition used herein is dissolved in an appropriate solvent to exhibit viscosity. Meanwhile, some of the materials exhibiting viscosity may exhibit viscosity when melted by heat. In order to maximize one of the advantages of the present invention, such as a non-heating process, a material used as the viscous composition exhibits viscosity when dissolved in an appropriate solvent.

The solvent which is used to prepare the viscous composition by dissolving a viscous material is not particularly limited, and water, anhydrous or hydrous lower alcohols having 1 to 4 carbon atoms, acetone, ethyl acetate, chloroform, 1,3-butylene glycol, hexane, diethyl ether, or butyl acetate may be used as the solvent.

According to an embodiment of the present invention, the viscous material further contains a drug. A microneedle is one of main uses of the microstructure of the present invention, and is used for the purpose of transdermal administration. Therefore, the drug is added to the biocompatible material during the preparing procedure of the viscous composition.

The drug that can be used herein is not particularly limited. For example, the drug includes chemical drugs, protein medicines, peptide medicines, nucleic acid molecules for gene therapy, nanoparticles, and active ingredients and cosmetic ingredients for functional cosmetics.

Examples of the drug usable herein may include anti-inflammatory agents, pain relievers, anti-arthritic agents, antispasmodics, anti-depressive agents, antipsychotics, tranquilizers, anti-anxiety, drug, narcotic antagonists, anti-Parkinson's disease drugs, cholinergic agonists, anti-cancers, anti-angiogenic agents, immunosuppressive agents, antiviral agents, antibiotics, appetite suppressants, pain relievers, anti-cholinergic agents, anti-histamines, anti-migraine agents, hormonal agents, coronary, cerebral or peripheral vasodilators, contraceptives, anti-thrombotic agents, diuretics, antihypertensive agents, cardiovascular therapeutic agents, and cosmetic ingredients (e.g., anti-wrinkle agent, skin aging inhibitor, and skin whitening agent), but are not limited thereto.

According to an embodiment of the present invention, the microstructure according to the present invention is manufactured under non-heating treatment conditions or at room temperature or at a low temperature lower than the room temperature (e.g., 5 to 20□). Therefore, according to the present invention, even when the drug used herein is a heat-sensitive material, such as a protein medicine, a peptide medicine, or a nucleic acid molecule for gene therapy, it is possible to manufacture a microstructure involving the drug.

According to an embodiment of the present invention, the method of the present invention is used to manufacture a microstructure involving a heat-sensitive drug, for example, a protein medicine, a peptide medicine, or vitamin (preferably, vitamin C).

The protein/peptide medicine involved in the microstructure by the method of the present invention is not particularly limited, and examples thereof may include hormones, hormone analogues, enzymes, enzyme inhibitors, signaling proteins or fragments thereof, antibodies or fragments thereof, single chain antibodies, binding proteins or binding domains thereof, antigens, adhering proteins, structural proteins, regulatory proteins, toxin proteins, cytokines, transcription factors, blood coagulation factors, and vaccines, but are not limited thereto. In more detail, the protein/peptide drugs include insulin, IGF-1 (insulin-like growth factor 1), growth hormone, erythropoietin, G-CSFs (granulocyte-colony stimulating factors), GM-CSFs (granulocyte/macrophage-colony stimulating factors), interferon alpha, interferon beta, interferon gamma, interlukin-1 alpha and beta, interlukin-3, interlukin-4, interlukin-6, interlukin-2, EGFs (epidermal growth factors), calcitonin, ACTH (adrenocorticotropic hormone), TNF (tumor necrosis factor), atobisban, buserelin, cetrorelix, deslorelin, desmopressin, dynorphin A (1-13), elcatonin, eleidosin, eptifibatide, GHRH-II (growth hormone releasing hormone-II), gonadorelin, goserelin, histrelin, leuprorelin, lypressin, octreotide, oxytocin, pitressin, secretin, sincalide, terlipressin, thymopentin, thymosine α1, triptorelin, bivalirudin, carbetocin, cyclosporin, exedine, lanreotide, LHRH (luteinizing hormone-releasing hormone), nafarelin, parathyroid hormone, pramlintide, T-20 (enfuvirtide), thymalfasin and ziconotide.

According to an embodiment of the present invention, the viscous material further includes energy. In this case, the microstructure may be used to transfer or deliver energy, such as heat energy, light energy, or electrical energy. For example, with respect to photodynamic therapy, the microstructure may be used to induce light to a specific site of the human body, so that the light can be applied directly to tissues or the light can be applied to intermediates such as light-sensitive molecules.

The substrate for accommodating the viscous composition is not particularly limited, but may be formed of materials, such as polymers, organic chemicals, metals, ceramics, and semiconductors.

According to an embodiment of the present invention, the viscous composition is placed in a drop shape on the substrate. That is, the viscous composition may be dropped in a drop shape on the substrate According to another embodiment, the viscous composition may be coated on the substrate (see FIG. 9). The microstructure may be manufactured in a non-contact manner by coating the viscous composition on the substrate without forming drops and then applying negative pressure thereto.

The manufacturing of the substrate and the applying of the viscous composition to the substrate may be variously performed. According to an embodiment, the substrate or the viscous composition is patterned, thereby preventing the loss of the drug as much as possible. A representative embodiment will be described as follows.

According to a first embodiment, physical patterns are formed by forming grooves at predetermined intervals in a substrate. In this case, the viscous composition containing a drug is coated or dropped on the physically patterned regions, and thus, when the viscous composition is transformed into a microstructure shape by the negative pressure in step (b), the amount of viscous composition in the others except the patterned regions is minimized, thereby reducing the loss of the drug.

According to a second embodiment, the substrate is designed to be patterned into a hydrophilic region and a hydrophobic region. In this case, the viscous composition is coated or dropped on an easily attachable region of the substrate due to hydrophobic or hydrophilic characteristics thereof. For example, the hydrophilic type viscous composition is mainly coated or dropped on a hydrophilic region of the substrate. In addition, even when the viscous composition is entirely coated or dropped on the substrate, the viscous composition can gather in the easily attachable region, thereby reducing the loss of the drug.

According to a third embodiment, both the first embodiment and the second embodiment are employed. In this case, the substrate has physically formed grooves, so that the viscous composition is ready to be patterned. The viscous composition gathers in the patterned regions depending on the gravitational influence and chemical features of the hydrophilic or hydrophobic viscous composition even when the viscous composition is entirely coated or dropped, thereby reducing the loss of the viscous composition containing a drug.

According to a fourth embodiment, a hydrophilic or hydrophobic viscous composition not containing a drug is first coated or dropped on a general substrate, and a hydrophobic or hydrophilic viscous composition containing a drug is entirely coated or dropped thereon so that the viscous composition is patterned. In this case, the viscous composition not containing a drug and the viscous composition containing a drug are not well mixed due to different chemical properties thereof, and the low end of the microstructure does not penetrate the skin when an actually completed microstructure is applied to the skin, and thus a lower end forming region of the microstructure does not contain the drug, thereby reducing the unnecessary loss of the drug.

Step (b): Manufacturing of Microstructure by Application of Negative Pressure

Then, a negative pressure is applied to the viscous composition to induce an extension of the viscous composition, thereby manufacturing a microstructure.

As used herein, the term "negative pressure" refers to a condition where a pressure no higher than the atmospheric pressure is applied. For example, the negative pressure used herein includes 1-100,000 Pa, 10-100,000 Pa, 10-50,000 Pa, 10-40,000 Pa, 10-30,000 Pa, 10-20,000 Pa, 10-10,000 Pa, 10-5,000 Pa, 10-1,000 Pa, and 10-500 Pa.

When the negative pressure is applied to the viscous composition, the viscous composition is extended, and thus a microstructure, particularly, a shape of a microneedle is formed.

The applying of the negative pressure may be performed through various methods known in the art.

According to an embodiment of the present invention, the applying of the negative pressure is performed using a suction pipe which is connected with a negative pressure generator and has a suction port.

FIG. 1 shows a specific embodiment of an apparatus for manufacturing a microstructure according to the present invention. In FIG. 1, reference numeral 11 represents a negative pressure generator, e.g., a vacuum pump. The negative pressure generated by the vacuum pump is applied to a viscous composition through a suction pipe 12 openly connected with the vacuum pump 11 and a suction port 121 of the suction pipe 12, thereby inducing an upward extension of the viscous composition. The apparatus for manufacturing a microstructure may include a unit capable of adjusting the intensity of the negative pressure, the height of the suction pipe (i.e., the separation distance between the suction port and the viscous composition), the position of the suction pipe, the rise rate of the suction pipe, the position of a substrate (i.e., the position of the viscous composition), and the like. In addition, the apparatus for manufacturing a microstructure may include a sensor for sensing the start of the upward extension of the viscous composition to allow the suction pipe to rise at a predetermined rate. In addition, the apparatus for manufacturing a microstructure may include a temperature sensor for adjusting the manufacturing temperature of the microstructure.

As used to describe the negative pressure applying device herein, the term "suction pipe" includes all types of suction units which are openly connected with the negative pressure generator and capable of applying a negative pressure. For example, the suction pipe may be formed in a cylindrical, rectangular, or circular shape having one or a plurality of suction ports.

FIG. 2 shows a specific embodiment of the present invention in which the microstructure is manufactured using the suction pipe. When the suction pipe is close to a viscous composition (e.g., a viscous solution drop), the negative pressure is strongly applied to the viscous composition, so that the viscous composition starts an upward extension thereof. The suction pipe is slowly raised at the time when the extension occurs, and thus the viscous composition is transformed into a microstructure, particularly, a microneedle. The suction pipe is stopped at a predetermined height, and the shape of the microstructure is maintained while the negative pressure is continuously applied. In this case, the drying may be performed while the shape of the microstructure is maintained.

Herein, the extension of the viscous composition by the negative pressure includes an upward or downward extension of the viscous composition placed on the substrate. The viscous composition is extended upwards when the negative pressure is applied downwards, and extended downwards when the negative pressure is applied upwards. According to an embodiment of the present invention, the viscous composition is extended upwards.

According to an embodiment of the present invention, step (b) may be performed while the distance between the viscous composition and the suction port of the suction pipe is adjusted. By adjusting the distance between the viscous composition and the suction port of the suction pipe, microstructures having a variety of desired shapes and dimensions (e.g., diameter, effective length, aspect ratio, and hardness) can be manufactured.

According to an embodiment of the present invention, a plurality of suction pipes are used, and in this case, a plurality of microstructures are manufactured by step (b). As shown in FIG. 3, in cases where the suction pipe is fabricated such that a plurality of suction ports are arranged, a plurality of microstructures can be simultaneously manufactured.

According to an embodiment of the present invention, step (b) may be performed while the diameter of the suction ports is adjusted. As shown in FIG. 5, the shape and/or dimension of the microstructure can be varied depending on the diameter of the suction pipe. For example, the smaller the diameter of the suction port, the larger the aspect ratio of the microstructure may be.

According to an embodiment of the present invention, step (b) may be performed while the intensity of the negative pressure is adjusted (see FIG. 6). Microstructures having a variety of shapes and dimensions can be manufactured by adjusting the intensity of the negative pressure applied to the viscous composition. For example, the stronger the intensity of negative pressure, the higher the aspect ratio of the microstructure.

According to an embodiment of the present invention, step (b) may be performed while the shape of the suction pipe or suction port is adjusted. As shown in FIG. 7, microstructures having a variety of shapes and/or dimensions can be manufactured through the change in the shape of the suction pipe or suction port.

According to an embodiment of the present invention, step (b) may be performed while the rise rate or position of the suction pipe is adjusted (see FIG. 8).

In the present invention, the negative pressure may be applied to the viscous composition regardless of the position of the suction pipe. The suction pipe may be positioned above the viscous composition, and may be positioned partially below the viscous composition. According to an embodiment of the present invention, step (b) may be performed while the suction port of the suction pipe is attached (or closely contacted with) the substrate (see FIGS. 10 and 11). A single suction pipe may be applied to one viscous composition as shown in FIG. 10, or a single suction pipe may be applied to a plurality of viscous compositions as shown in FIG. 11.

According to an embodiment of the present invention, the method of the present invention may be performed while the temperature is adjusted.

According to an embodiment of the present invention, the present invention is performed at room temperature or at a low temperature lower than the room temperature. The temperature for performing the present invention is not particularly limited, but the optimal performance can be exhibited even at room temperature or low temperatures. This advantageous feature can minimize the loss of drug activity due to the high temperature in the conventional art, and the manufacturing procedure and apparatus can be simplified.

According to an embodiment of the present invention, the shape and/or dimension of the finally manufactured microstructure can be adjusted by a freezing procedure (adjusting the time to freeze) of the viscous composition (e.g., a biodegradable polymeric material solution) through the adjustment of the temperature.

According to an embodiment of the present invention, step (b) may be performed while the airflow at the suction port is adjusted. The shape and/or dimension of the manufactured microstructure can be verified by adjusting the line and/or rate of the airflow.

According to an embodiment of the present invention, step (b) may be performed while the upward extension rate (or growth rate) of the viscous composition is adjusted.

According to an embodiment of the present invention, the method of the present invention may be performed while the surface features of the substrate are adjusted.

According to an embodiment of the present invention, the present invention can be applied to manufacture a microstructure having a plurality of layers.

For example, step (a) includes the following sub-steps of: (a-1) coating a first viscous composition on the substrate and applying negative pressure to the first viscous composition, thereby forming a support layer; and (a-2) spotting a second viscous composition on the support layer, wherein step (b) is performed by applying a negative pressure to the second composition spotted on the support layer, thereby forming a microstructure having two layers.

In this case, the first viscous composition and the second viscous composition are formed of the same material or different materials.

According to an embodiment of the present invention, the viscous compositions may be spotted on the second viscous composition in a single layer or several layers.

Optionally, step (a) includes the following sub-steps of: (a-1) placing a first viscous composition in a drop shape on the substrate and applying negative pressure to the first viscous composition, thereby forming a support layer; and (a-2) spotting a second viscous composition on the support layer, wherein step (b) is performed by applying negative pressure to the second composition spotted on the support layer, thereby forming a microstructure having two layers.

In this case, the first viscous composition and the second viscous composition are formed of the same material or different materials.

According to an embodiment of the present invention, the viscous compositions may be spotted on the second viscous composition in a single layer or several layers.

This microneedle with a plurality of layers can be utilized to improve the delivery efficiency and adjust the delivery amount of drugs.

According to an embodiment of the present invention, step (b) may be performed using a suction port having a plurality of holes with a predetermined shape, interval, or both. In this case, the flow of the fluid and the negative pressure can be adjusted, and as a result, a microneedle with an adjusted shape and/or dimension can be manufactured.

According to an embodiment of the present invention, step (b) is performed while the cross-sectional shape of the suction pipe is adjusted. In this case, a microneedle with an adjusted shape and/or dimension (e.g., a diameter and aperture ratio of a top) can be manufactured.

According to an embodiment of the present invention, step (b) is performed while the position and angle of the suction port with respect to the viscous composition are adjusted, thereby manufacturing a microstructure with a bent shape. Through this, the direction, angle, and shape of the top of the manufactured microstructure can be adjusted.

According to an embodiment of the present invention, in step (b), the solidifying also occurs simultaneously with the extension of the viscous composition. That is, while the viscous composition is extended by the application of the negative pressure, the solidifying also occurs, and thus the microstructure can be manufactured at the same time when the extension is completed. Without wishing to be bound by theory, a pressure drop condition formed in the viscous composition by the application of the negative pressure is determined to promptly solidify the extended viscous composition exposed to the air. This feature enables the microstructure to be promptly and conveniently manufactured by the present invention.

According to an embodiment of the present invention, a separate solidifying procedure (e.g., drying) is not needed after step (b). Optionally, the method of the present invention further includes a step of solidifying (e.g., drying) the microstructure after step (b). The conditions for drying are not particularly limited, and include any condition under which moisture is removed from the microstructure. For example, the solidifying may be performed through drying at room temperature or freeze-drying.

FIG. 17 shows an embodiment of a procedure in which, after the shape of the microstructure is molded by the application of the negative pressure, the residual moisture is removed through an additional drying process, according to the present invention. The drying is performed under various conditions, such as vacuum or freezing conditions. Through this, the strength of the microstructure is enhanced and the moisture is removed from the microstructure, thereby improving the stability of the microstructure.

According to an embodiment of the present invention, the method of the present invention may be entirely or partially performed in a non-contact manner. According to an embodiment, the method of the present invention is entirely performed in a non-contact manner. As used herein, the term "non-contact manner" refers to the manufacturing of the microstructure by inducing an extension of the viscous composition without attaching a structure to the viscous composition. That is, the extension of the viscous composition according to the present invention may be performed without the aid of any structure. In addition, according to an embodiment of the present invention, the present invention is performed without an intervention of a solid or liquid between the viscous composition and the suction pipe of the negative pressure applying unit. For example, the viscous composition is placed on the substrate under an ambient atmosphere, and the suction pipe is spaced apart from the viscous composition. In addition, an outer part of the suction pipe is placed under an ambient atmosphere, like the viscous composition, and an inner part of the suction pipe is openly connected to the negative pressure generator. Thus, when the negative pressure is generated, the viscous composition is under the influence of the negative pressure.

One of the most important features of the present invention is that the microstructure can be manufactured in a non-contact type without contact with any other structure, such as a mold or pillar. This can overcome the loss, which is generated due to a separating procedure from the contacted structure or a cutting procedure through physical destruction after the molding of the microstructure is completed, and the restriction of the manufacturing yield. Furthermore, the non-contact type manufacturing has an effect that the microstructure can be manufactured on various surfaces.

The present invention can provide various microstructures, and for example, a microneedle, microblade, microknife, microfiber, microspike, microprobe, microbarb, microarray, or microelectrode can be provided.

According to another aspect of the present invention, the present invention provides a microstructure manufactured by the method of the present invention.

The top of the microstructure of the present invention has a diameter of 1-500 μm, 2-300 μm, or 5-100 μm, and an effective length of 100-10,000 μm, 200-10,000 μm, 300-8,000 μm, or 500-2,000 μm. As used herein, the term "top" of the microstructure refers to one end with the minimum diameter in the microstructure. As used herein, the term "effective length" refers to a vertical length from the top of the microstructure to the surface of the support.

Advantageous Effects

Features and advantages of the present invention are summarized as follows:

(i) The present invention is directed to a method for manufacturing a microstructure by application of the negative pressure without heat treatment, and this method has not been adopted in the conventional art.

(ii) According to the present invention, the method can be performed under room temperature or low-temperature conditions, unlike existing methods for manufacturing a microstructure. Through the method of the present invention, various materials which are sensitive to heat and thus easily destroyed or transformed can be mounted on the microstructure. Thus, the applicable fields of a microneedle can be further expanded.

(iii) According to the present invention, the microstructure can be manufactured in a non-contact manner without contact with any other structure which has been used in the conventional art, such as a mold or pillar. This can overcome the loss and the restriction of the manufacturing yield, which are incurred due to a separating procedure from the contacted structure or a cutting procedure through physical destruction after the molding of the microstructure is completed. Furthermore, the non-contact type manufacturing method has an effect that the microstructure can be manufactured on various surfaces.

(iv) The present invention can produce a microstructure with a desired shape and dimension (e.g., diameter, effective length, aspect ratio, and hardness) through a comparatively rapid and convenient process. This feature enables the mass production and quality control of the microstructure.

(v) The present invention can provide microstructures with various shapes and/or dimensions by adjusting the intensity of the negative pressure, the diameter of the suction port, the shape of the suction pipe or suction port, the rise rate or position of the suction pipe, the airflow at the suction port, the manufacturing temperature, the surface property of the substrate, and/or the upward extension rate of the viscous composition.

(vi) According to an embodiment of the present invention, while the viscous composition is extended by application of negative pressure, the solidifying occurs, and thus the microstructure can be manufactured at the same time when the extension is completed. Therefore, the microstructure can be manufactured more promptly and conveniently by the present invention.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1

As a negative pressure providing device, a suction pipe connected to a vacuum pump (GSOV-550, Kae Seong Scientific) was used. As a viscous composition for manufacturing a microstructure, hyaluronic acid (Soliance) was used. 800 mg of hyaluronic acid (molecular weight: 29 kDa) was dissolved in 20 ml of deionized distilled water to prepare a 40% (w/v) solution.

Figure 18:
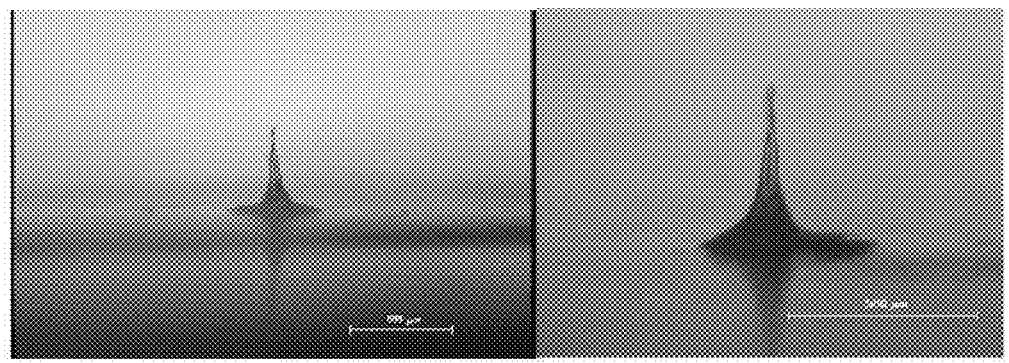
FIG. 18 shows images of the formation of microneedles according to the invention.
Figure 19:
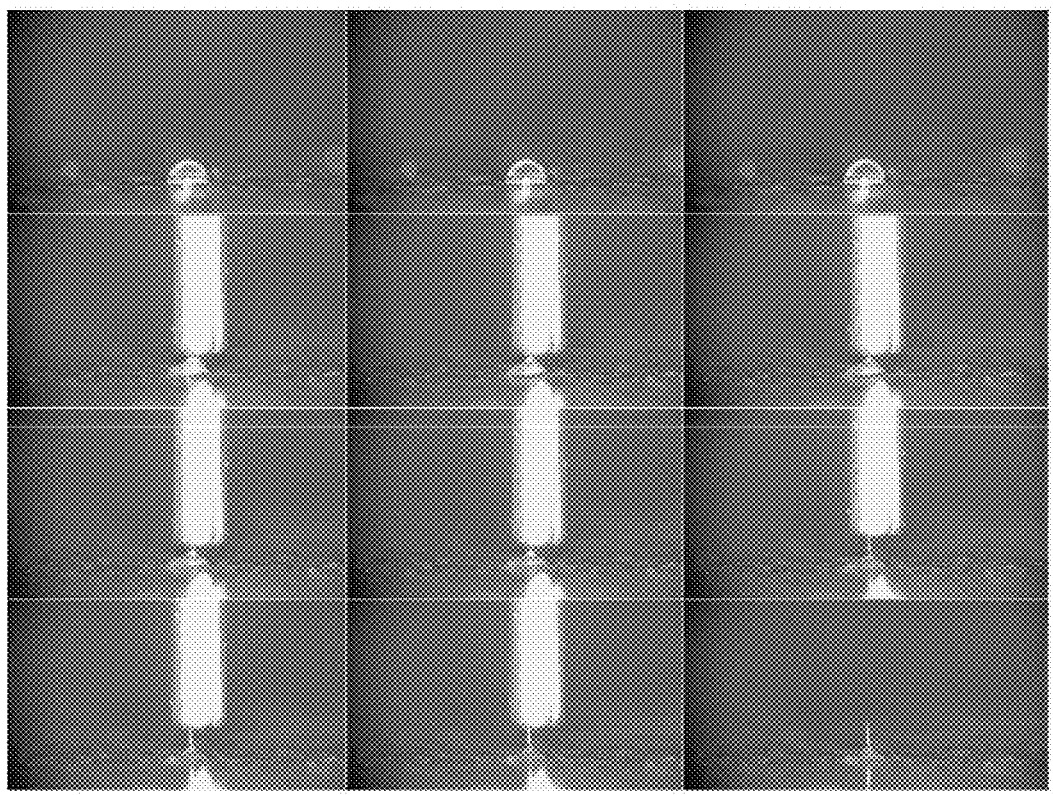
FIG. 19 shows images obtained by photographing the manufacturing procedure of the invention by lapse of time.

A drop of the 40% hyaluronic acid viscous solution was formed on a glass substrate. A suction port of the suction pipe was placed directly above the viscous solution drop, and the negative pressure (20,000 Pa) was applied. At the time when the shape of the viscous solution drop was transformed by the negative pressure, the suction pipe was raised at a rate of 5 mm/sec to extend the viscous solution drop, thereby molding a microneedle. In cases where the suction port was not raised, microneedles with short lengths or distorted shapes were formed. The suction was stopped in a state in which the suction was raised and the shape of the microneedle was maintained through suction. Then, the viscous solution was promptly solidified through the pressure drop due to the suction, thereby finally obtaining a microneedle (see FIG. 18). Meanwhile, FIG. 19 shows images obtained by photographing the manufacturing procedure of the present invention by lapse of time.

Example 2

Figure 20A:
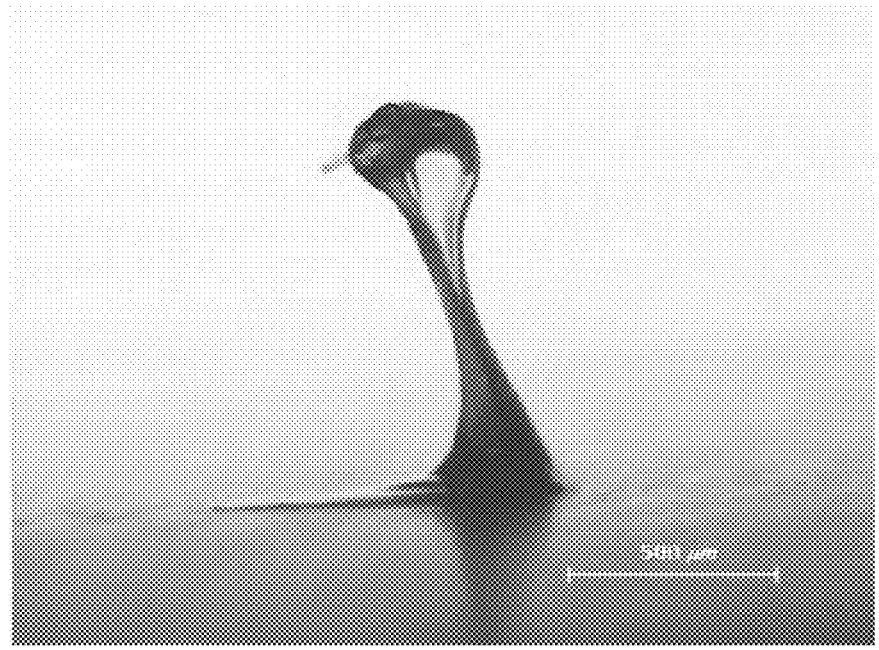
FIG. 20A shows an image of a microstructure manufactured when the intensity of the negative pressure was not sufficient.
Figure 20B:
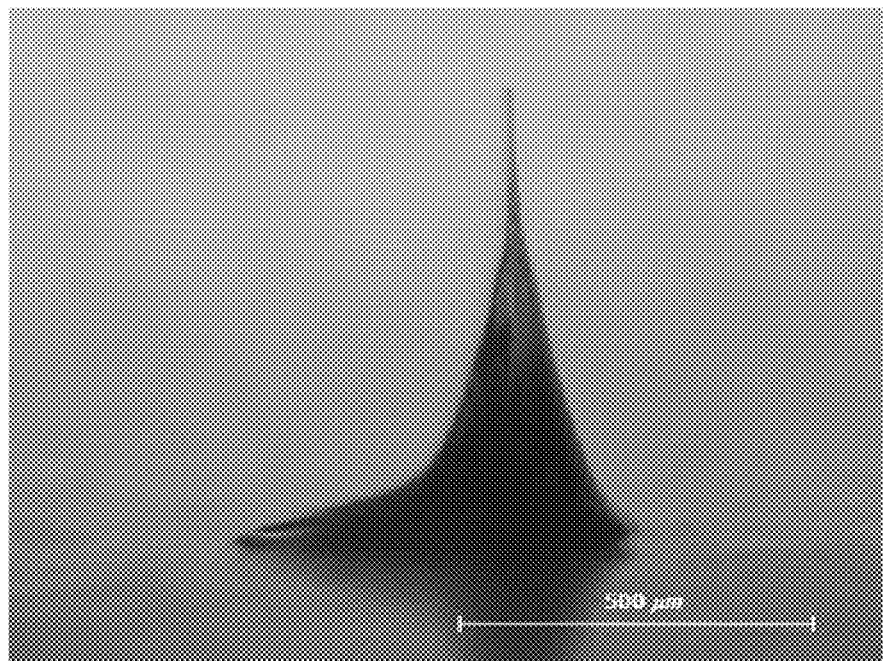
FIG. 20B shows an image of a microstructure manufactured when sufficient negative pressure was provided.

A microstructure was manufactured by the same method as in Example 1, except that a 33% (w/v) solution of hyaluronic acid (molecular weight: 29 kDa) was used and the intensity of the negative pressure was adjusted. FIG. 20a is an image of a microstructure manufactured when the intensity of the negative pressure was not sufficient (70,000 Pa), and shows that the extension (transformation) of the viscous composition only reached halfway up the structure, and thus a thin structure was not formed. FIG. 20b is an image of a microstructure manufactured when a sufficient negative pressure (20,000 Pa) was provided, and shows that a microneedle was formed such that the extension (transformation) of the viscous composition reached the top of the structure.

Example 3

A microstructure was manufactured by the same method as in Example 1, except that a 33% (w/v) solution of hyaluronic acid (molecular weight: 29 kDa) was used. The hardness of the manufactured microstructures was measured using the Universal testing machine (ZO.5TN, Zwick). As a result of measuring the hardness, the microstructure manufactured by the present invention had a hardness of 0.36 N, which is enough to penetrate the skin to function as a microneedle.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

DRAWING LEGEND INSERTION

Figure 1:
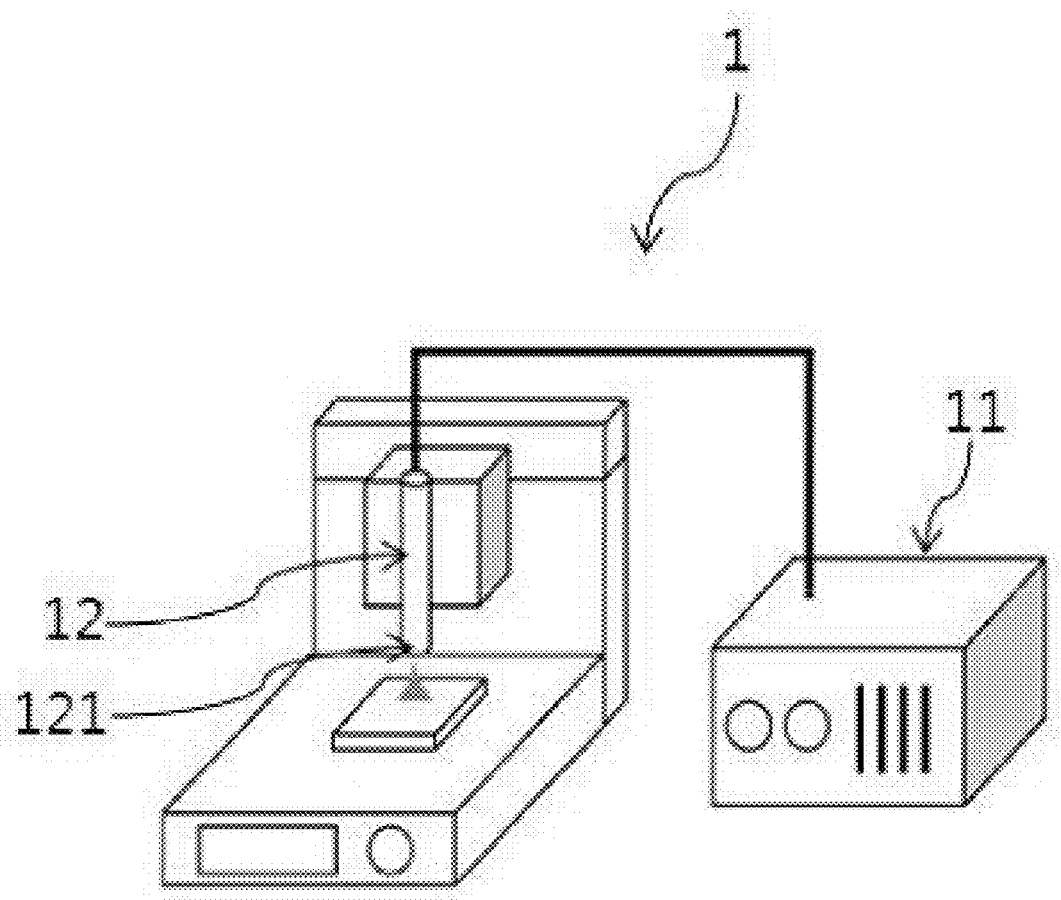
FIG. 1 shows an apparatus, 1, for manufacturing a microstructure according to the present invention. Reference numeral 11 represents a negative pressure generator, e.g., a vacuum pump. Reference numeral 12 represents a suction pipe, while reference numeral 121 represents a suction port.
Figure 2:
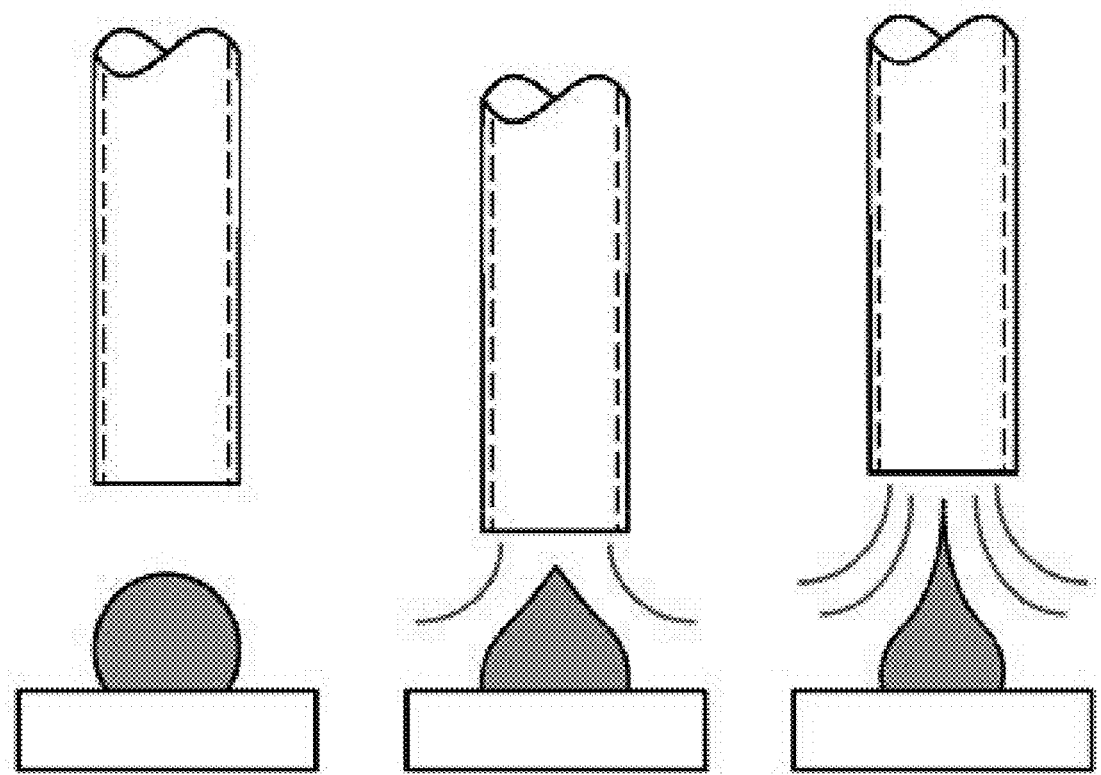
FIG. 2 shows a specific embodiment of the invention in which a microstructure is manufactured using a suction pipe.
Figure 3:
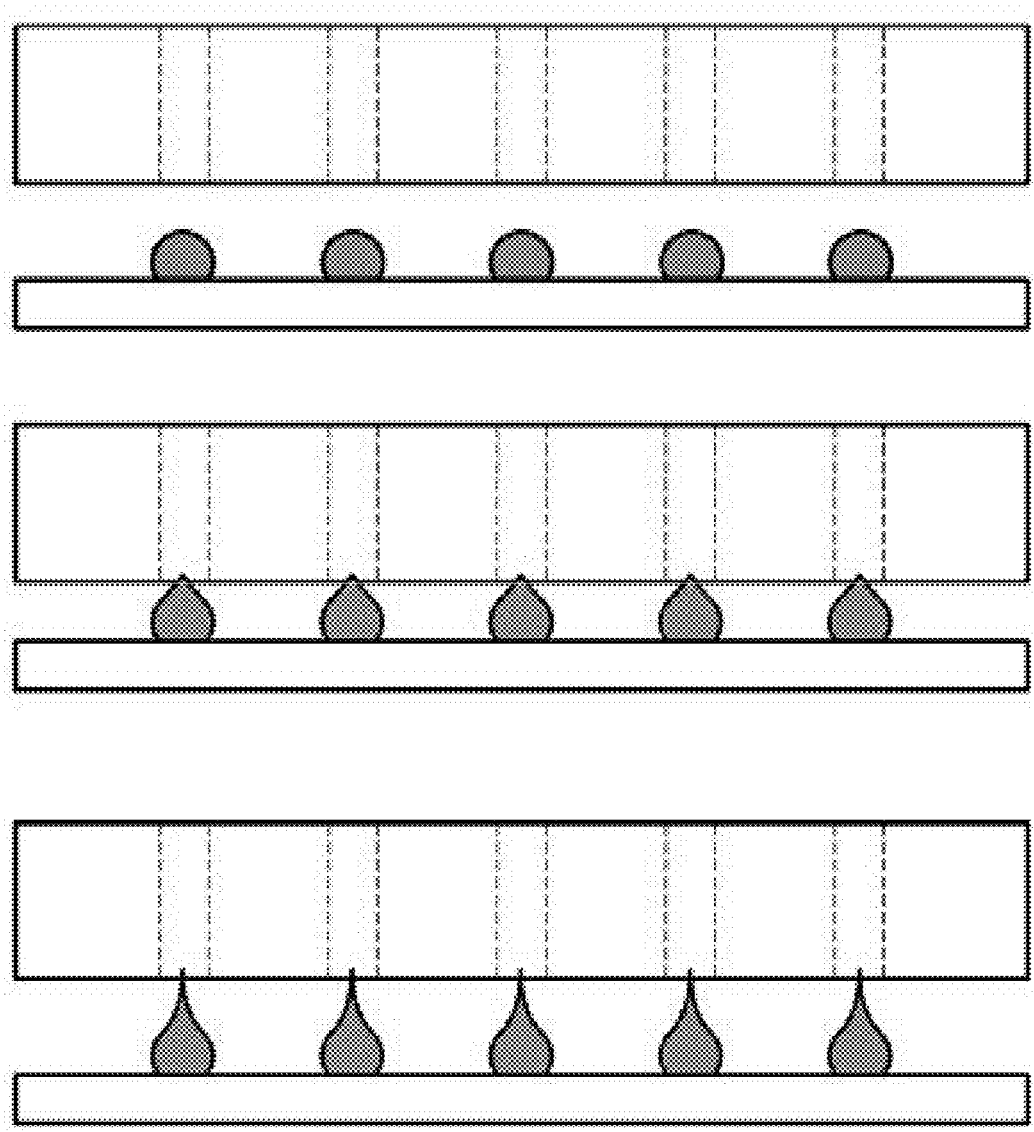
FIG. 3 shows a specific embodiment of the invention in which a plurality of suction pipes are used.
Figure 4:
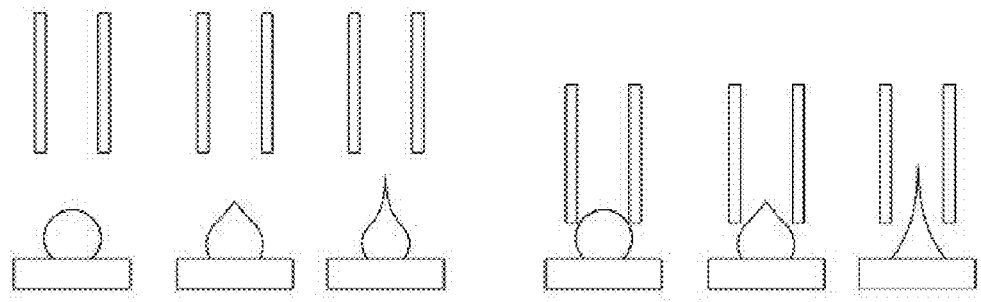
FIG. 4 shows a specific embodiment of the invention in which the distance between the suction port of the suction pipe and the viscous composition is adjusted.
Figure 5:
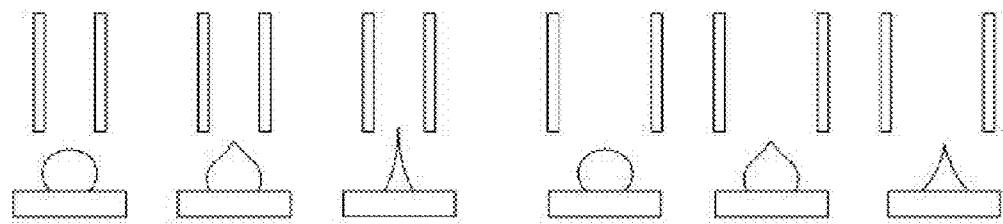
FIG. 5 shows a specific embodiment of the invention in which the diameter of the suction port is adjusted.
Figure 6:
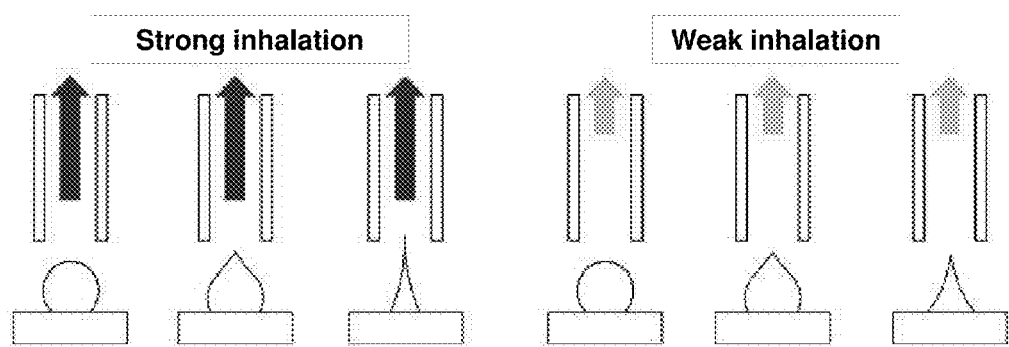
FIG. 6 shows a specific embodiment of the invention in which the intensity of the negative pressure is adjusted.
Figure 7:
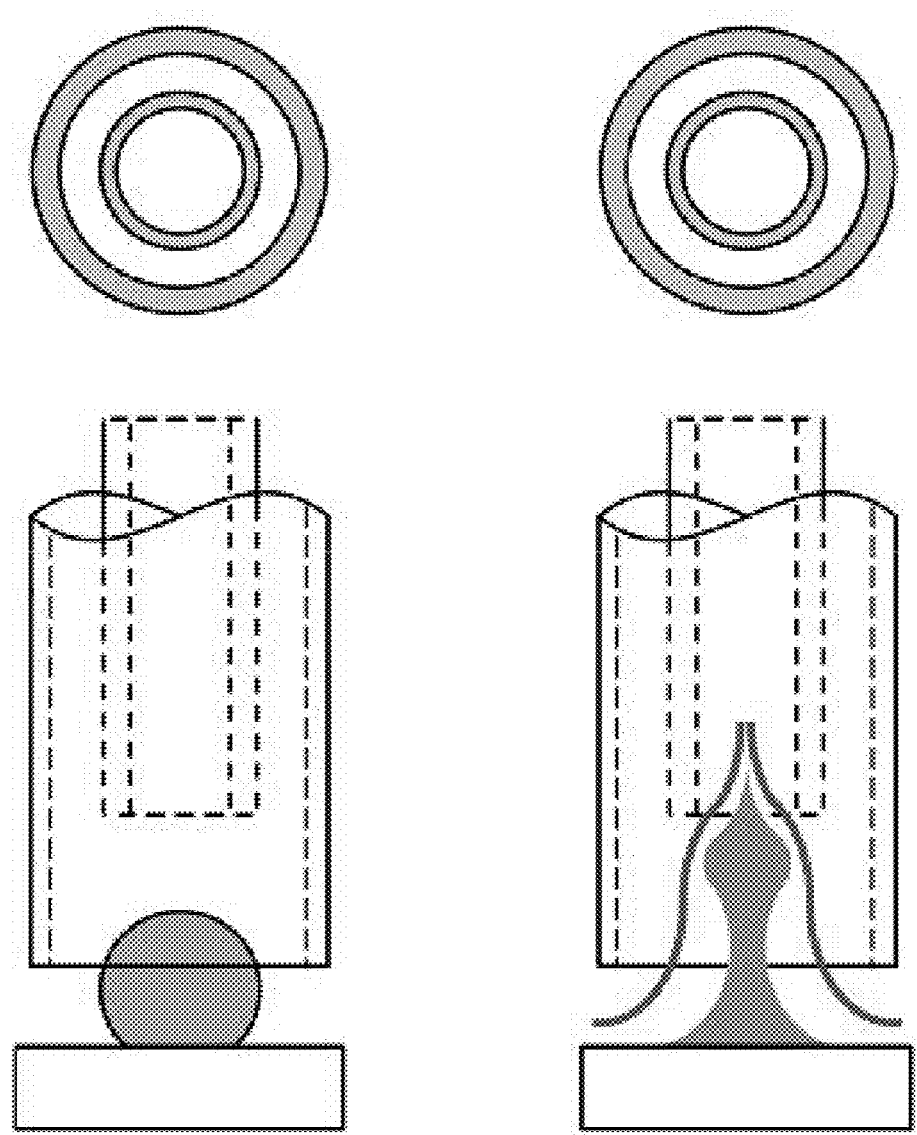
FIG. 7 shows a specific embodiment of the invention in which the shape of the suction pipe or the suction port is adjusted.
Figure 8:
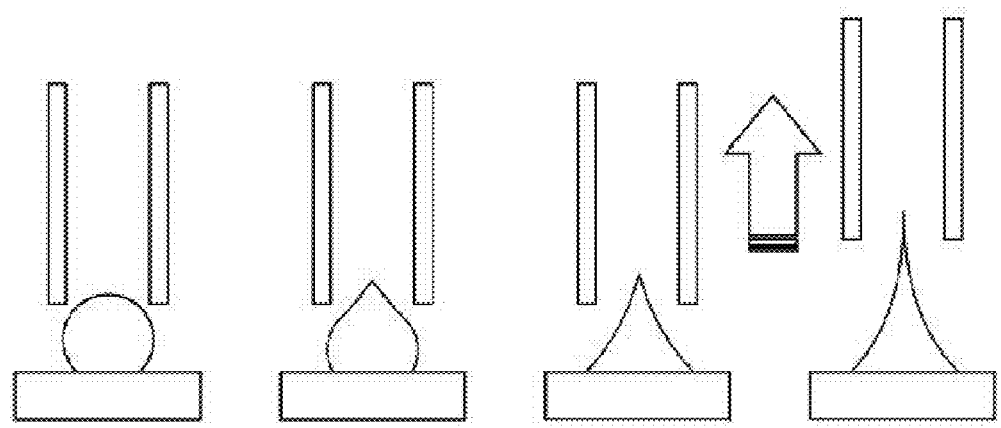
FIG. 8 shows a specific embodiment of the invention in which the rise rate or position of the suction pipe is adjusted.
Figure 9:
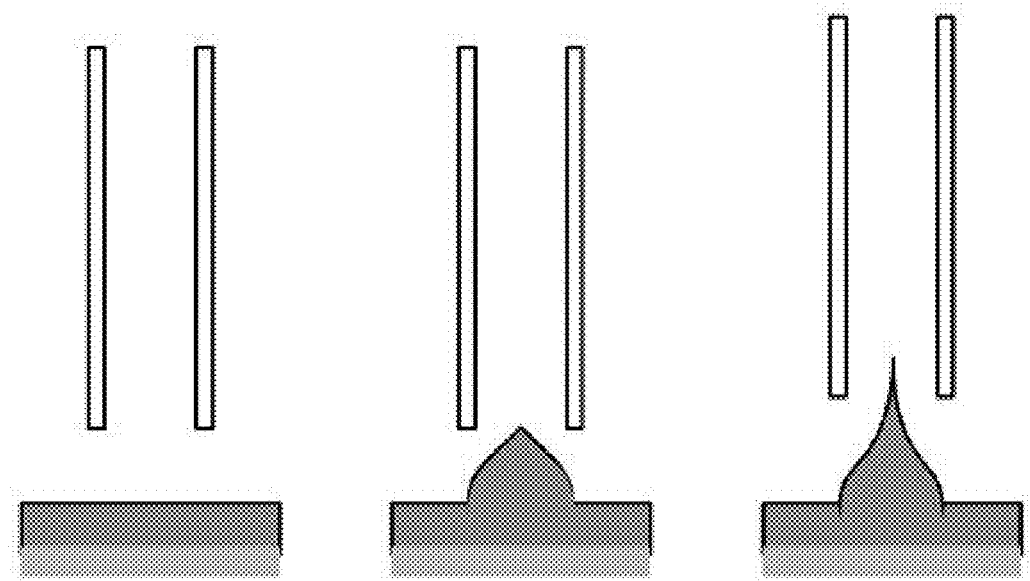
FIG. 9 shows a specific embodiment of the invention in which the viscous composition is spread on the substrate.
Figure 10:
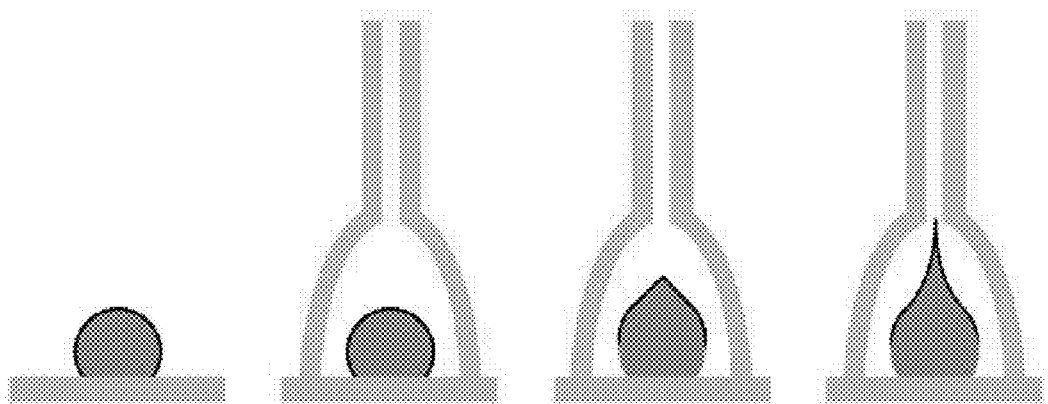
FIG. 10 shows a specific embodiment of the invention in which the suction port of the suction pipe is attached to (or closely contacted with) the substrate.
Figure 11:
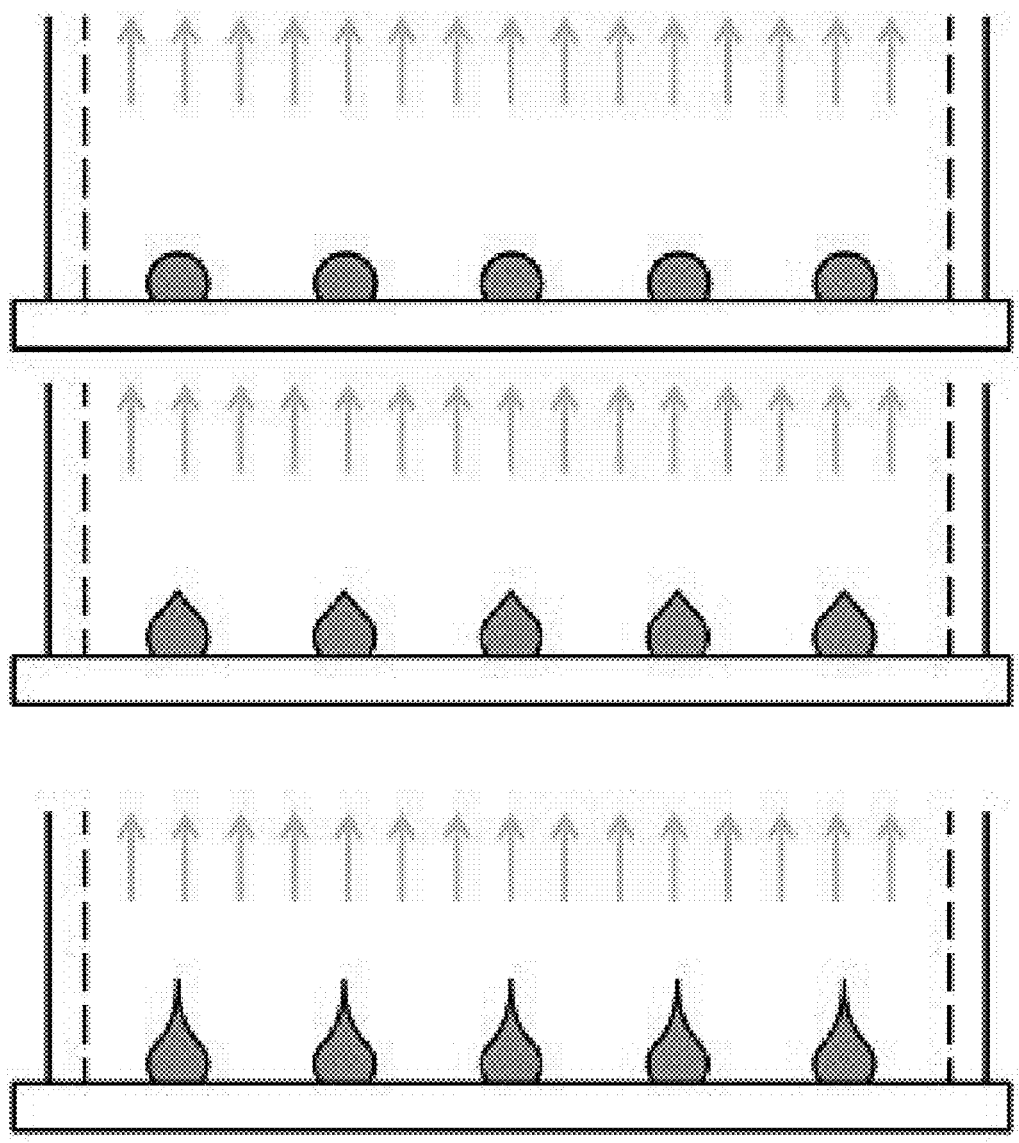
FIG. 11 shows an alternative specific embodiment of the invention in which the suction port of the suction pipe is attached to (or closely contacted with) the substrate.
Figure 12:
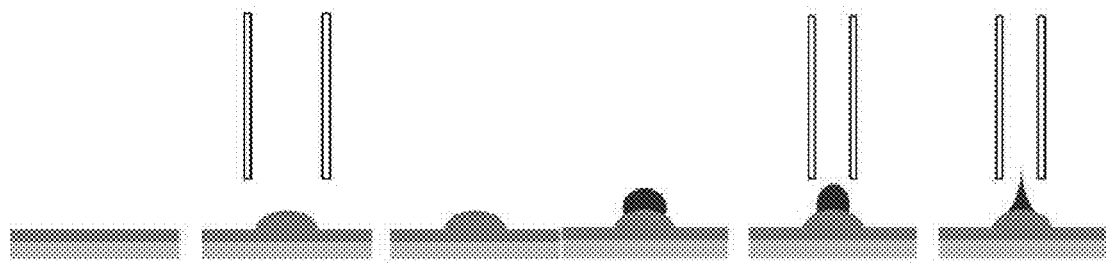
FIG. 12 shows a specific embodiment of the invention in which a first viscous composition is applied to a substrate to form a support layer, a second viscous composition is spotted on the support layer, and a negative pressure is applied to the second viscous composition.
Figure 13:
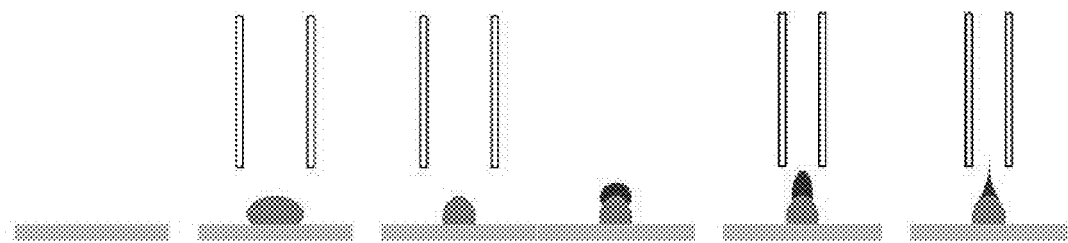
FIG. 13 shows a specific embodiment of the invention in which a first viscous composition is applied to a substrate, a negative pressure is applied to the first viscous composition to form a support layer, a second viscous composition is spotted on the support layer, and a negative pressure is applied to the second viscous composition.
Figure 14:
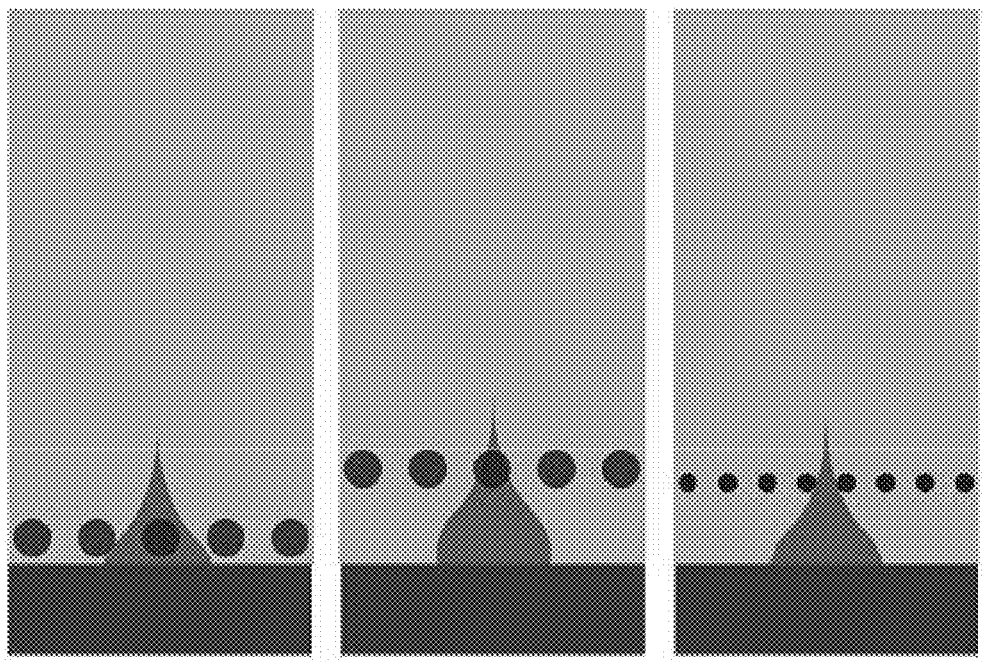
FIG. 14 shows a specific embodiment of the invention in which a suction port having a plurality of holes with a predetermined shape, interval, or both, is used.
Figure 15A:
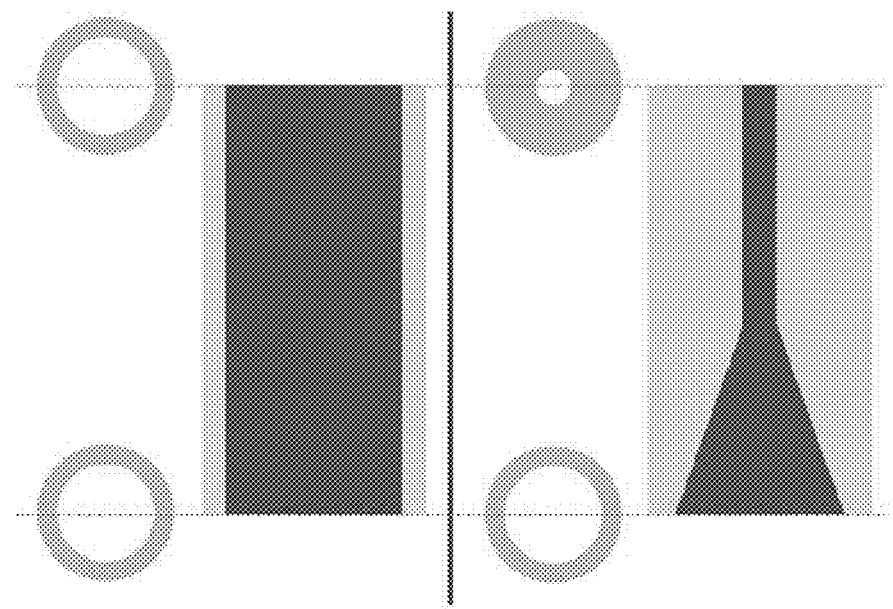
FIG. 15A and FIG. 15B show a specific embodiment of the invention in which the cross-sectional shape of the suction pipe is adjusted.
Figure 15B:
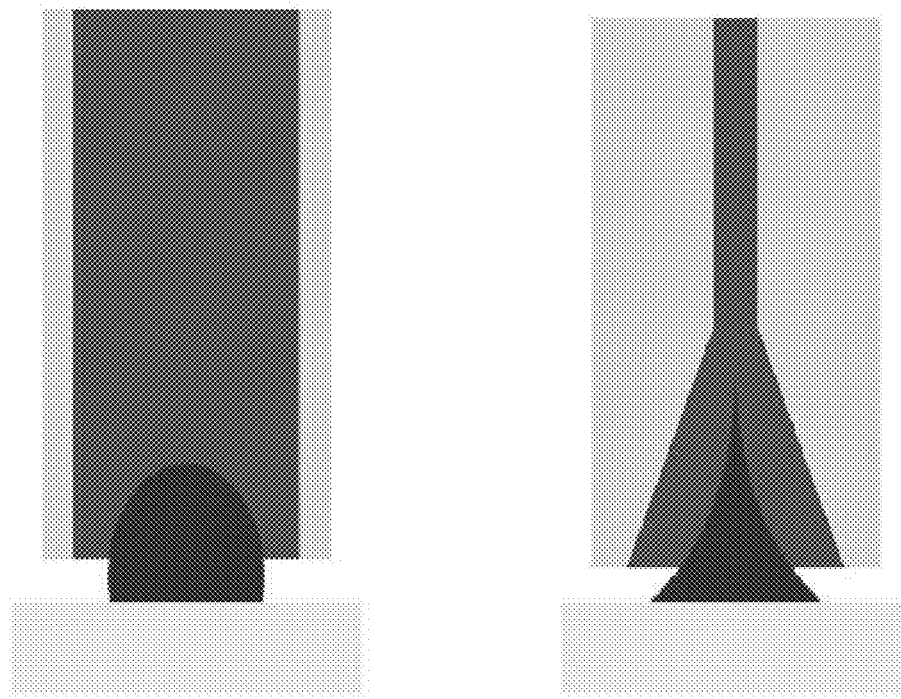
Figure 16:
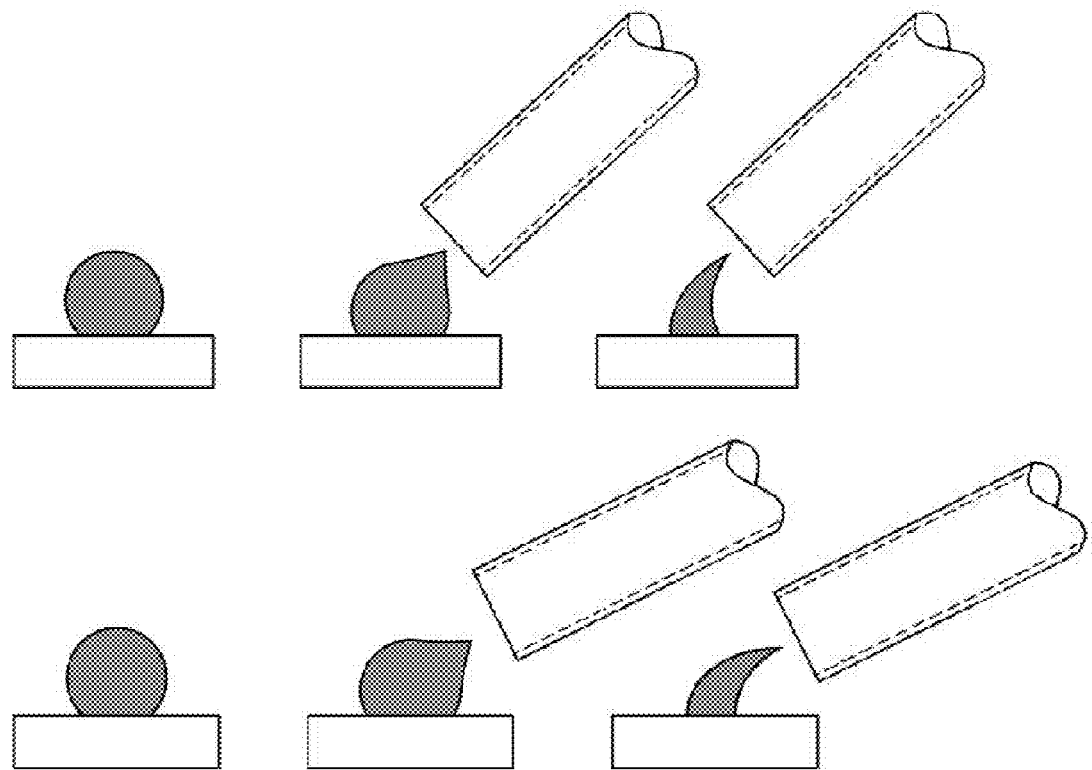
FIG. 16 shows a specific embodiment of the invention in which the position and angle of the suction port with respect to the viscous composition is adjusted.
Figure 17:
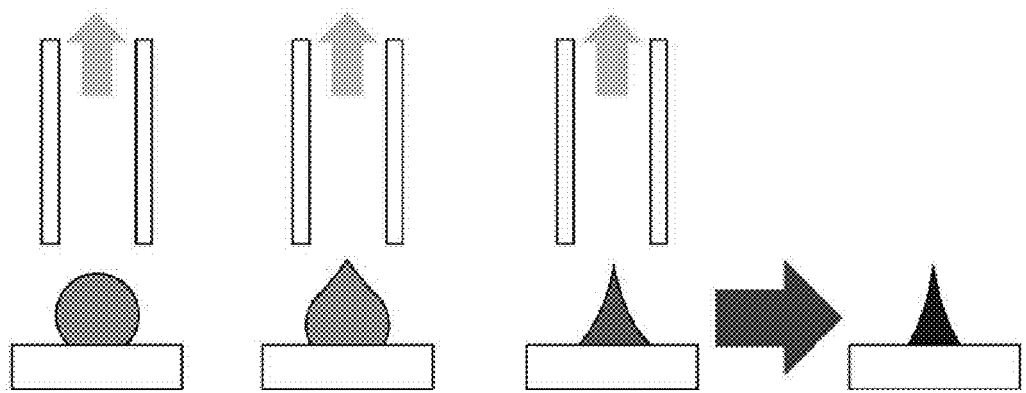
FIG. 17 shows a specific embodiment of the invention in which, after the shape of the microstructure is molded by the application of negative pressure, the residual moisture is removed through an additional drying process.

FIG. 6
Strong suction
Weak suction

The invention claimed is:

1. A method for manufacturing a microstructure, the method comprising:
   (a) placing a viscous composition on a substrate; and
   (b) applying negative pressure to the viscous composition to induce an extension of the viscous composition, thereby forming a microstructure,
   wherein step (b) is performed using a suction pipe having a suction port, and step (b) is performed while the suction port is spaced apart from the viscous composition wherein in step (b), solidification occurs simultaneously to extension.

2. The method of claim 1, wherein the viscous composition includes a biocompatible or biodegradable material.

3. The method of claim 1, wherein the viscous composition is placed in a drop shape on the substrate.

4. The method of claim 1, wherein the applying of the negative pressure is performed using the suction pipe connected to a negative pressure generator.

5. The method of claim 4, wherein the suction port is spaced upward from the viscous composition and, in step (b), the distance between the viscous composition and the suction port of the suction pipe is adjusted.

6. The method of claim 4, wherein the suction pipe includes a plurality of suction pipes, which are used to manufacture a plurality of microstructures.

7. The method of claim 4, wherein in step (b), the diameter of the suction port is adjusted.

8. The method of claim 1, wherein in step (b), the intensity of the negative pressure is adjusted.

9. The method of claim 4, wherein in step (b), the shape of the suction pipe or suction port is adjusted.

10. The method of claim 4, wherein in step (b), at the time when the shape of the viscous composition is changed by applying the negative pressure to the viscous composition using the suction pipe, the suction pipe is raised at a predetermined rate.

11. The method of claim 10, wherein in step (b), the rise rate or position of the suction pipe is adjusted.

12. The method of claim 4, wherein step (b) is performed while the suction port of the suction pipe is attached to the substrate in no contact with an inner surface of the suction pipe.

13. The method of claim 1, wherein the method is performed at room temperature or at a low temperature lower than the room temperature.

14. The method of claim 4, wherein in step (b), the airflow at the suction port is adjusted.

15. The method of claim 1, wherein in the method, the temperature is adjusted.

16. The method of claim 1, wherein in step (b), the extension rate of the viscous composition is adjusted.

17. The method of claim 1, wherein in the method, the surface property of the substrate is adjusted.

18. The method of claim 1, wherein step (a) includes the following sub-steps of:
 (a-1) coating a first viscous composition on the substrate and applying negative pressure to the first viscous composition, thereby forming a support layer; and
 (a-2) spotting a second viscous composition on the support layer, wherein step (b) is performed by applying negative pressure to the second composition spotted on the support layer, thereby forming a microstructure having two layers.

19. The method of claim 1, wherein step (a) includes the following sub-steps of:
 (a-1) placing a first viscous composition in a drop shape on the substrate and applying negative pressure to the first viscous composition, thereby forming a support layer; and
 (a-2) spotting a second viscous composition on the support layer, wherein step (b) is performed by applying negative pressure to the second composition spotted on the support layer, thereby forming a microstructure having two layers.

20. The method of claim 4, wherein step (b) is performed using the suction pipe having a suction port with a plurality of holes which have a predetermined shape, interval, or shape and interval.

21. The method of claim 4, wherein in step (b), the cross-sectional shape of the suction pipe is adjusted.

22. The method of claim 1, wherein the microstructure is a microneedle, a microspike, a microblade, a microknife, a microfiber, a microprobe, a microbarb, a microarray, or a microelectrode.

* * * * *